United States Patent
Koken et al.

(10) Patent No.: US 7,217,413 B1
(45) Date of Patent: May 15, 2007

(54) USE OF NOVEL AGENTS INDUCING CELL DEATH IN SYNERGY WITH INTERFERONS

(75) Inventors: Marcel Koken, Paris (FR); Frédérique Quignon, Paris (FR); Hugues De The, Paris (FR); Jean-Claude Ameisen, Paris (FR); Frédéric De Bels, Paris (FR)

(73) Assignees: Institut de la Sante et de la Recherde Medicale (INSERM), Paris (FR); Centre National de la Recherche Scientifique (CNRS), Paris (FR)

( * ) Notice: Subject to any disclaimer, the term of this patent is extended or adjusted under 35 U.S.C. 154(b) by 0 days.

(21) Appl. No.: 09/744,605

(22) PCT Filed: Jul. 30, 1999

(86) PCT No.: PCT/FR99/01901

§ 371 (c)(1),
(2), (4) Date: Jul. 27, 2001

(87) PCT Pub. No.: WO00/07616

PCT Pub. Date: Feb. 17, 2000

(30) Foreign Application Priority Data

Jul. 31, 1998 (FR) .................................. 98 09886

(51) Int. Cl.
*A61K 33/36* (2006.01)
*A01K 38/00* (2006.01)
*A01K 38/21* (2006.01)

(52) U.S. Cl. ............... 424/85.4; 424/620; 424/621; 424/624; 514/2; 514/21

(58) Field of Classification Search ............... 514/2, 514/21; 424/620, 621, 623, 85.4
See application file for complete search history.

(56) References Cited

U.S. PATENT DOCUMENTS 6,733,792 B1 * 5/2004 Lu .............................. 424/620
2002/0001841 A1 * 1/2002 Kaltoft et al.

FOREIGN PATENT DOCUMENTS

WO  PCT/CN98/00118   11/1999
WO  WO 02/18572    *  3/2002

OTHER PUBLICATIONS

Zhu, et al., Proc Natl Acad Sci U S A Apr. 15, 1997;94(8):3978-83.*
U.S. Appl. No. 60/091,684.*
Gianni et al (Blood, Jun. 1, 1998, vol. 91, pp. 4300-4310).*
Bazarbachi et al (Blood, Jan. 1, 1999, vol. 93, pp. 278-283).*
Chelbi-Alix et al (Leukemia, 1995, vol. 9, pp. 2027-2033).*
Zhu et al (PNAS, 1997, vol. 94, pp. 3978-3983).*
He et al (Anticancer Research, 1997, vol. 17, No. 5C, p. 3927, abstract #6).*
Muller et al (EMBO, Jan. 2, 1998, vol. 17, pp. 61-70).*
Chelbi-Alix et al (NATO ASI Series H: Cell Biology (1996, vol. 99 (Tumor Biology), pp. 17-27).*
Chen et al (blood, vol. 88, pp. 1052-1061).*
Albert et al (Nature, Mar. 5, 1998, vol. 392, pp. 86-89).*
Lutz et al (Trends in Immunology, 2002, vol. 23, pp. 445-449).*
Sauter et al (Journal of Experimental Medicine, 2000, vol. 191, pp. 423-433).*
Perry et al (Biotechniques, 1997, vol. 22, pp. 1102-1106).*
Takahashi et al, Oncogene, 2004, vol. 23, pp. 2819-2824.*
Wadia and Dowdy, Advanced Drug Delivery Reviews, 2005, vol. 57, pp. 579-596.*
Johnson and Tracey, 'Peptide and Protein Drug Delivery', In: Encyclopedia of Controlled Drug Delivery, vol. 2, 1999, pp. 816-833.*
Lallemand-Breitenbach et al, Journal of Experimental Medicine, 2001 vol. 193, pp. 1361-1371.*
Xiang, BAX-induced cell death may not require interleukin 1—converting enzyme-like proteases, Proc. Natl. Acad. Sci. USA, vol. 93, pp. 14559-14563, Dec. 1996, Cell Biology.
Quignon, PML induces a novel caspase-independent death process, Nature Genetics, vol. 20, pp. 259-265, Nov. 1998.
Vercammen, Inhibition of Caspases Increases the Sensitivity of L929 Cells to Necrosis Mediated by Tumor Necrosis Factor, J. Exp. Med., The Rockefeller University Press, vol. 187, No. 9, pp. 1477-1485, May 4, 1998.
Griffith, CD95-Induced Apoptosis of Lymphocytes in an Immune Privileged Site Induces Immunological Tolerance, Immunity, vol. 5, pp. 7-16, Jul. 1996.
Voll, Immunosuppressive effect of apoptotic cells, Nature, vol. 390, pp. 360-361, Nov. 27, 1997.
Gao, Antiinflammatory Effects of CD 95 Ligand (FasL)-induced Apoptosis, J. Exp. Med., The Rockefeller University Press, vol. 188, No. 5, pp. 887-896, Sep. 7, 1998.
Melcher, Tumor immunogenicity is determined by the mechanism of cell death via induction of heat shock protein expression, Nature Medicine, vol. 4, No. 5, pp. 581-587, May 1998.
Byrd, Old and New Therapies in Chronic Lymphocytic Leukemia: Now Is the Time for a Reassessment of Therapeutic Goals, Seminars in Oncology, vol. 24 (1), pp. 65-74, Feb. 1998.
Soignet, Clinical and laboratory studies in leukemia of an organic arsenical melarsoprol, Proc. of ASCO, vol. 16, pp. 4A, 1997.
Konig, Comparative Activity of Melarsoprol and Arsenic Trioxide in Chronic B-Cell Leukemia Lines, Blood, vol. 90 (2), pp. 562-570, Jul. 15, 1997.
Slee, Benzyloxycarbonyl-Val-Ala-Asp (OMe) fluoromethylketone (Z-VAD.FMK) inhibits apoptosis by blocking the processing of CPP32, Biochem. J., vol. 315, pp. 21-24, 1996.

* cited by examiner

*Primary Examiner*—Karen A. Canella
(74) *Attorney, Agent, or Firm*—Browdy & Neimark, PLLC

(57) ABSTRACT

The invention concerns the use of novel agents including cell death, and in particular, an agent for overexpression of the PML protein on nuclear bodies, combined with interferons, to induce the death of undesirable cells and simulate an immune reaction.

8 Claims, 7 Drawing Sheets

USE OF NOVEL AGENTS INDUCING CELL DEATH IN SYNERGY WITH INTERFERONS

The present invention relates to the use of novel agents inducing cell death, and in particular of an agent allowing the overexpression of the PML protein on nuclear bodies, in combination with interferons, to induce the death of undesirable cells.

Nuclear bodies are structures associated with the nuclear matrix, of unknown function, and which contain a number of proteins including PML, Sp100, ISG20, PIC-1/SUMO-1, lysp100, PLZF, Int-6, CBP, Rb, RFP and the ribosomal P protein (Lamond et al., 1998). The gene encoding the PML (for "ProMyelocytic Leukemia") protein was identified from its fusion with the RARα (retinoic acid nuclear receptor) gene in the t(15;17) translocation found in patients suffering from acute promyelocytic leukaemia (APL). This *PML* gene is a target gene for inteferons, and its overexpression causes stoppage of the growth of certain cell lines (Koken et al., 1995). In malignant APL cells, the PML protein is not located on the nuclear body but delocalized because of the expression of PML-RARα. Arsenic oxide induces the return of PML to its normal location as well as the death of the cell. In normal non-APL cells, where the location of PML is normal, arsenic induces the aggregation of PML towards large modified bodies, but the phenomenon is not accompanied by cell death (Zhu et al., 1997).

The authors of the invention have now discovered that the overexpression of the PML protein located on the nuclear bodies causes the death of the cell through a novel mechanism defferent from that of apoptosis induced by caspases.

The major consequence of this discovery is that a substance promoting the targeting of the PML protein to the cellular bodies and/or its stabilization is particularly useful for inducing the death of undesirble cells.

The said substance which induce the targeting of the PML protein to the nuclear bodies and/or its stabilization may be identified by standard tests known to a person skilled in the art, it being possible for the measurement of the intracellular transit between the cytoplasmic and nucleoplasmic fractions and the fraction associated with the nuclear bodies and the stabilization of the PML protein to be carried out in particular by Western blotting.

The said undesirable cells may be in particular cells of a tumour, cells infected with a virus, a parasite or a bacteria, immune cells participating in an inappropriate immune reaction, genetically modified cells, senescent or hyperplasic cells.

The expression "tumour" is understood to mean any undesirable, benign or malignant cell proliferation including in particular solid cancers and leukaemias and lymphomas. Among the malignant tumours, there may be mentioned in particular chronic myeloid leukaemias and adult T lymphoid leukaemias (ATL) and melanomas.

The subject of the present invention is therefore the use of at least one substance promoting the targeting of the PML protein towards the nuclear bodies and/or its stabilization, for the production of a medicament intended to induce the death of undesirable cells.

The expression of the PML protein being induced by interferons, the presence of interferons, whether of endogenous origin or administered to the patient simultaneously or sequentially, is necessary for the efficacy of the treatment envisaged.

Surprisingly, the authors of the present invention have more particularly discovered that zVAD (benzyloxycarbonyl-Val-Ala-Asp(O-methyl) fluoromethyl ketone), on the one hand, stabilizes the PML protein and, on the other hand, accelerates cell death induced by the interferons.

However, zVAD is initially known as an inhibitor of caspases, which are proteases involved in the apoptosis process (Salvesen et al., 1997). Studies (McCarthy et al., 1997) have in addition shown that zVAD prevented or greatly delayed cell death. The discovery by the authors of the present invention, according to which zVAD does not block cell death induced by the interferons but, on the contrary, accelerates it, is therefore in disagreement with the results which could be expected by persons skilled in the art.

The subject of the present invention is more particularly the use of a caspase inhibitor and/or substrate, such as zVAD, for the production of a medicament intended to induce the death of undesirable cells. The acceleration of cell death which is observed may be a consequence of the stabilization of PML but may also involve other mechanisms, which remain within the framework of the present invention.

The expression "caspase substrate" is understood to mean any compound capable of binding to caspases.

The authors of the present invention have also discovered that arsenic, and more particularly arsenic trioxide, on the one hand, promotes the targeting of the PML protein towards cellular bodies and, on the other hand, accelerates cell death induced by interferons.

The subject of the present invention is more particularly the use of a compound of arsenic or of a compound having the same biological properties as arsenic, for the production of a medicament intended to induce the death of undesirable cells, in association with at least one interferon.

This induction of cell death which is observed may be a consequence of the targeting of the PML protein towards the cellular bodies, but may also involve other mechanisms, which remain within the framework of the present invention.

Among the compounds of arsenic, there may be mentioned in particular arsenic trioxide or melarsoprol.

The expression "compound having the same biological properties as arsenic" is understood to mean any compound which, like arsenic, is an inhibitor of phosphatase and/or is capable of creating covalent adducts by binding with dithiol groups.

The caspase inhibitors and/or substrates or the compounds of arsenic or the compounds having the same biological properties as arsenic are preferably used to induce the death of the undesirable cells, in association with the PML protein, and/or with an agent inducing the overexpression of the PML protein. Among the agents inducing the overexpression of the PML protein, an interferon, such as α-, β- or γ-interferon, is preferably used.

Indeed, the authors of the present invention have more particularly discovered that the caspase substrates, in particular zVAD, as well as the compounds of arsenic, in particular arsenic trioxide, acted in synergy with the interferons to induce and accelerate cell death.

The simultaneous or sequential administration of PML or of an agent inducing the overexpression of the PML protein, such as the interferons, may be unnecessary if the quantity of PML or of agent inducing the overexpression of the PML protein, such as the interferons, of endogenous origin, is sufficient. Nevertheless, according to a preferred embodiment of the invention, the administration of a substance chosen from the compounds of arsenic, the compounds having the same biological properties as arsenic and the caspase inhibitors and/or substrates, is associated with a simultaneous or sequential administration of PML protein, and/or of an agent inducing the overexpression of the PML protein, such as the interferons.

Forming part of the invention is the use of a substance chosen from the compounds of arsenic, the compounds having the same biological properties as arsenic and the caspase inhibitors and/or substrates, in association with an interferon, to induce the death of undesirable cells, whether it is mediated by the PML protein induced by the said interferon or by another mechanism also induced by the said interferon.

The subject of the present invention is also a method of therapeutic treatment in which a therapeutically effective quantity of at least one substance chosen from the compounds of arsenic, the compounds having the same biological properties as arsenic and the caspase inhibitors and/or substrates are administered to a patient requiring such a treatment, in association with a pharmaceutically acceptable vehicle.

Preferably, a therapeutically effective quantity of PML protein, and/or of an agent inducing the overexpression of the PML protein, such as an interferon, is also administered to the said patient, simultaneously or sequentially.

The subject of the present invention is also a pharmaceutical composition containing 1) either at least one caspase inhibitor and/or substrate combined with:

at least one compound of arsenic or one compound having the same biological properties as arsenic;

and/or the PML protein and/or at least one agent inducing the overexpression of the PML protein, such as an interferon;

in the presence of a pharmaceutically acceptable vehicle;

2) or at least one compound of arsenic or one compound having the same biological properties as arsenic, associated with the PML protein and/or with at least one agent inducing the overexpression of the PML protein, such as an interferon, in the presence of a pharmaceutically acceptable vehicle.

The subject of the present invention is also a kit comprising a) a pharmaceutical composition (1) containing at least one caspase inhibitor and/or substrate, in association with a pharmaceutically acceptable vehicle;

and/or a pharmaceutical composition (2) containing at least one compound of arsenic or one compound having the same properties as arsenic, in association with a pharmaceutically acceptable vehicle; and b) a pharmaceutical composition (3) containing the PML protein in association with a pharmaceutically acceptable vehicle;

and/or a pharmaceutical composition (4) containing at least one agent inducing the overexpression of the PML protein, such as an interferon, in association with a pharmaceutically acceptable vehicle;

the said pharmaceutical compositions being intended for simultaneous or sequential administration.

The mode of administration and the dosage depend on the condition treated and its state of progression, as well as the weight, age and sex of the patient.

In accordance with the invention, the formulation of the medicaments of the invention allows administration in particular by the oral, anal, nasal, intramuscular, intradermal, subcutaneous or intravenous route.

The dose for administration envisaged may be for example from 1 to 50 mg per day, preferably by the intravenous route, for the compounds of arsenic, from 1 to 250 mg per kg of body weight of caspase substrates such as zVAD, and from 1 to 20 millions of international units (M IU), preferably from 3 to 5 M IU, preferably by the intramuscular or subcutaneous route, per day or every two days, for interferon.

The authors of the invention have, in addition, discovered that the cell death induced by the overexpression of the PML protein located on the nuclear bodies has different characteristics from the apoptosis induced by caspases. In the case of the cell death induced by PML, the nuclear morphological characteristics typical of apoptosis, such as condensation of chromatin and nuclear fragmentation, are in particular not observed.

Furthermore, whereas the cell death induced by the interferons alone exhibits the characteristics of apoptosis, the authors of the present invention observed that the synergistic association of zVAD with the interferons causes this apoptotic phenotype to disappear, the cell death then exhibiting characteristics different from those of apoptosis.

One of the major consequence of this discovery is the capacity of the undesirable cells killed by the mechanism induced by PML to cause an immune reaction against similar undesirable cells which would have escaped death mediated by the PML protein.

This property makes particularly advantageous the use of a substance chosen from the compounds of arsenic, the compounds having the same biological properties as arsenic, and the caspase inhibitors and/or substrates, preferably in combination with an interferon, to induce the death of undesirable cells, and/or to induce an immune reaction.

Thus, the administration of these medicaments will allow a form of immunotherapy, or of "vaccination", by causing a reaction of the immune system which removes the surviving undesirable cells, whether they are cancer cells, infected cells or any other undesirable cell which participates in the development of a disease.

This property is linked to the fact that these medicaments, in particular the association interferon and zVAD or zVAD alone, cause in the undesirable cells a phenomenon of death which does not posses all the characteristics of apoptosis, which is the most frequent physiological phenotype in cellular suicide.

In particular, the caspase inhibitor zVAD prevents the appearance of most of the manifestations of apoptosis, which depend on an activation, in the dying cell, of certain caspases. Indeed, while the caspases are not essential for the execution of cellular suicide, they appear, on the other hand, to be essential during the phenomena of cellular suicide, for the execution of an apoptotic death phenotype (Xiang J. et al., PNAS 1996, 93:14559; Quignon F. et al., Nature Genetics 1998, 20:259; Vercammen D. et al., J. Exp. Med. 1998, 187:1477).

A number of results suggest that the manner in which a cell dies plays an important role in the induction or otherwise of an immune reaction directed against the surviving cells possessing the same characteristics (including for example the nature of the abnormality which makes them cancerous, or the nature of the infectious agent which they contain).

The onset, in a cell, of a phenomenon of apoptotic death would have the effect of limiting the induction of an immune reaction against the surviving cells possessing the same characteristics, or even of promoting the induction of a form of immune tolerance, that is to say of a selective inhibition of the induction of an immune response directed against the surviving cells possessing the same characteristics. Results obtained in some particular models (in vitro or in vivo in the mouse eye anterior chamber), suggest that the apoptotic death of a cell could, in general, limit or inhibit the induction of delayed hypersensitivity type cell-mediated immune reactions (termed Th1) mediated by the CD4+ T lymphocytes (Griffith T. et al., Immunity 1996, 5:7; Voll R. et al., Nature 1997, 390:350; Gao Y. et al., J. Exp. Med. 1998, 188:887), a reaction which represents one of the essential manifestations of an effective immune reaction against undesirable cells.

In a particular model of tumours in mice, it has been shown that the onset, in cancer cells, of phenomena of apoptotic death does not bring about the induction of an effective immune reaction directed against the live cancer cells exhibiting the same characteristics, whereas the artificial introduction into these cancer cells of a gene which prevents the onset, in the dying cancer cells, of part of the apoptotic phenotype, allows the induction of an effective immune reaction directed against the live cancer cells exhibiting the same characteristics but into which this gene has not been artificially introduced (Melcher et al., 1998, Nature Med., vol. 4, No. 5, pp 581–597).

The discovery that the medicaments described in this application cause the death of undesirable cells while not causing (or while preventing) the onset, in the dying cells, of an apoptotic phenotype is therefore important. It implies that these medicaments would have the effect not only of causing the death of undesirable cells, but also of allowing the concomitant induction of an effective immune reaction allowing the concomitant or subsequent elimination of the undesirable cells which would have escaped the death induced by the medicaments.

This property may also be exploited for treating ex vivo a combination of cells which are likely to contain undesirable cells, before administration to a patient, for example a bone marrow preparation intended for a transplant in a leukaemia patient, such a preparation generally containing a few residual malignant cells. Such a treatment not only makes it possible to induce the death of the undesirable cells contained in the preparation, but also to cause an immune reaction directed against the undesirable cells present in the body of the patient to whom the treated cell preparation is administered.

The subject of the present invention is therefore also an in vitro method for inducing the death of undesirable cells comprising bringing undesirable cells into contact with a substance chosen from the compounds of arsenic, the compounds having the same biological properties as arsenic, and the caspase inhibitors and/or substrates, it being possible for the said substance to be preferably associated with the PML protein and/or with an agent inducing the overexpression of the PML protein, preferably an interferon.

The following examples and figures illustrate the invention without limiting the scope thereof.

LEGEND TO THE FIGURES

FIG. 1A represents the induction of the PML protein of 90 kD in a clone REF (T) PML, four hours after exposure to variable concentrations of $ZnCl_2$.

FIG. 1B represents a FACS analysis of REF (T) PML cells or of control cells, four hours 30 minutes after exposure to 150 μM of $ZnCl_2$. The left-hand panel represents the DNA content relative to the size of the cells. The right-hand panel represents the DNA content as a function of the fluorescence (TUNEL).

FIG. 1C represents the cytometric analysis of the REF (T) PML cells treated or otherwise with $ZnCl_2$, etoposide, or the caspase inhibitor zVAD. A labelling is carried out with Annexin V-FITC (left-hand panel) or Rhodamin 123 (right-hand panel). The percentage of apoptotic cells is indicated.

Figure 3A:
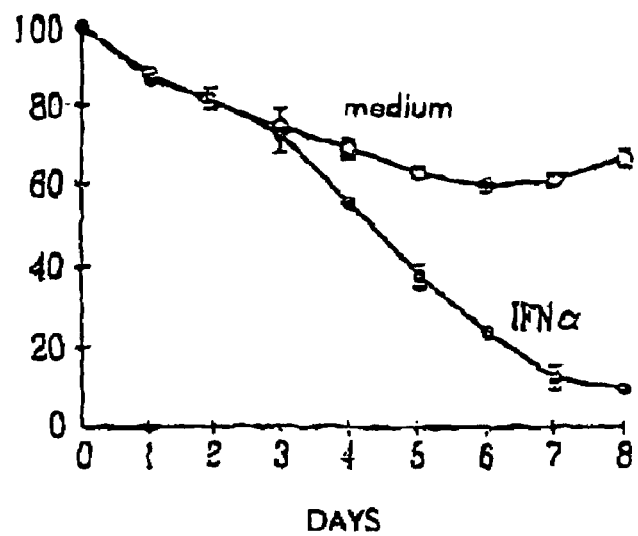

FIG 3A shows the survival of the monocytes treated with 1 000 U/ml of INFα. One representative experiment out of five is presented. The TUNEL tests demonstrate that the decrease in the cell count is due to apoptosis.

Figure 3B:
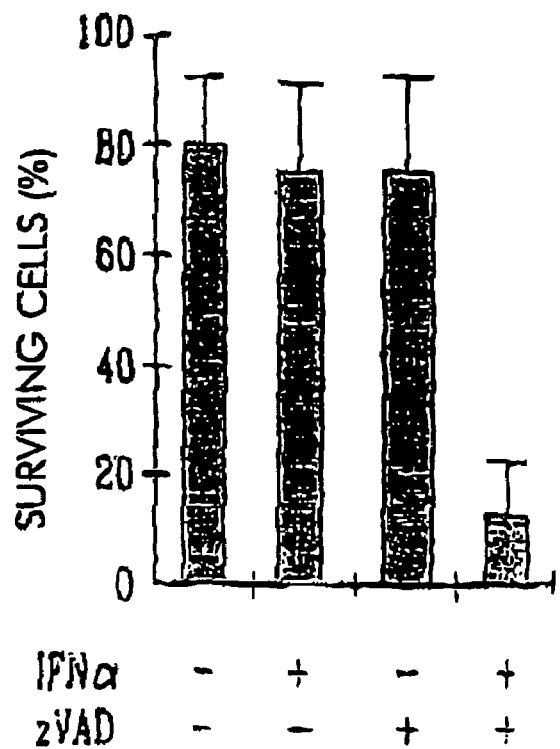

FIG. 3B represents histograms indicating the effect of zVAD (100 μM) 24 hours after its addition. The mean values ± standard deviation of 11 experiments are presented.

Figure 4A:
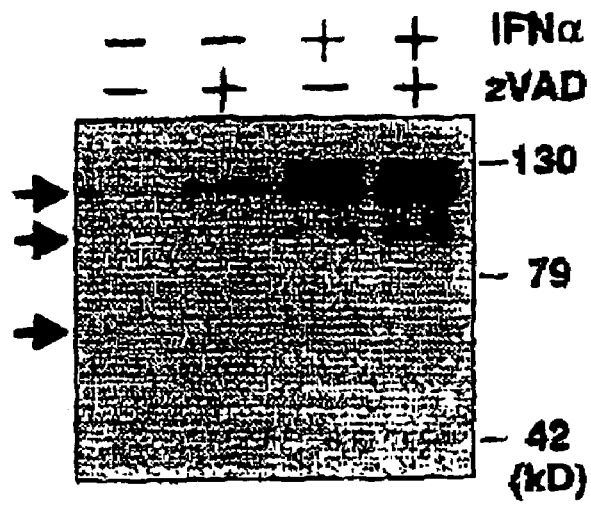

FIG. 4A shows that zVAD stabilizes the PML protein in the REF (T) cells.

Figure 4B:
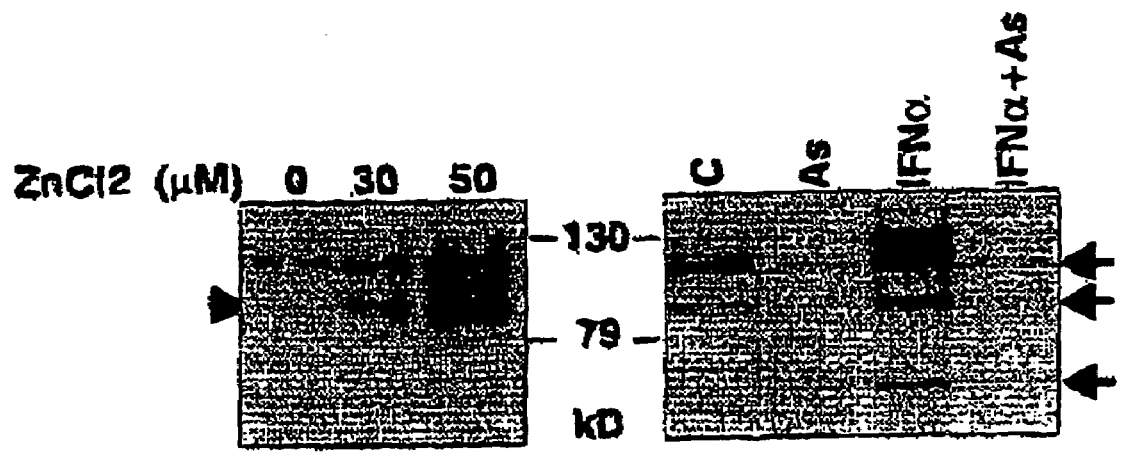

FIG. 4B shows that α-interferon (1 000 U/ml) induces rat PML in the REF (T) PML cells. The arrows indicate distinct isoforms of PML.

EXAMPLES

Materials and Methods

Plasmid Construct

A SacI-BglII fragment (−69, +55 base pairs) of the mouse metallothionein promoter was inserted into a plasmid pKS and was fused with a BglII-BamHI fragment of a PML cDNA leading to the plasmid pKSmMT-PML. For the GFP-PML fusion, the same PML fragment was inserted into the BglII site of the vector pEGFP-1 (Clontech). A retroviral vector expressing PML was also constructed by inserting a full-length cDNA for PML (de Théet al., 1991) into the EcoRI site of SRαtkneo (Muller et al., 1991).

Cell Culture

The REF (T) and MEF (T) cells are rat and mouse embryonic fibroblasts immortalized by an SV4DT expression vector. The REF (K1) cells are immortalized by an SV40T mutant which does not bind Rb, and the F111cells are spontaneously immortalized 3T3 rat fibroblasts. For clonogenicity tests, the cells were transfected with 10 μg of SRαtkneo-PML or SRαkneo on culture dishes 10 cm in diameter and selected with neomycin (500 μg/ml). To obtain inducible clones, a pool of RET (T) cells was cotransfected with the plasmid pKSmMt-PML and a hygromycin resistance vector (DSP-Hygro). The resistant colonies were examined for the expression of PML after four hours of treatment with $ZnCl_2$ (150 μM) and subjected to a second cycle of cloning by limiting dilution. Inducible CHO clones were constructed in a similar manner. The monocytes were prepared according to the method of Estaquier et al., 1997. Etoposide (used at 100 μM for 16 to 24 hours) was obtained from Biomol Research Laboratories, zVAD (benzyloxycarbonyl-Val-Ala-Asp fluoromethyl ketone, used at 250 μg/ml) is marketed by Bachem and rat IFNα by Access BioMedical. The human α-interferon was provided by Schering-Plough.

The antibodies against the human PML protein are described in the article by Daniel et al., 1993. The Western blot experiments with the endogenous rat PML protein were carried out with the monoclonal antibody 5E10 which detects both rat PML and human PML.

Evaluation of Cell Death

The cells were treated for 2 hours with 150 µM of $ZnCl_2$ (unless otherwise stated) in the presence or absence of heat-inactivated foetal calf serum, and then the cells were washed and incubated in a $ZnCl_2$-free medium. The TUNEL test was carried out according to the manufacturer's instructions (Boehringer Mannheim, kit for detection of cell death in situ), with the exception of the fixing step (4% formaldehyde in phosphate PBS buffer for 10 minutes). The cellular DNA content was evaluated by incubating for 10 minutes in propidium iodide at 50 µg/ml, in the presence of Rnase A at 100 µg/ml at 4° C. Analysis of the expression of phosphatidylserine on the outer sheet of the cell membranes was carried out using Annexin-V-fluos labelling (Boehringer Mannheim) and a loss of mitochondrial polarity with Rhodamin 123 (molecular probes) according to the manufacturer's instructions. The samples were analysed on a FACScan analyser (Lysis II software, Becton Dickinson). For the cleavage of the substrate with caspases, $5 \times 10^6$ cells were washed in PBS buffer, and incubated for one hour at 4° C. in 200 µl of lysis buffer (10 mM Hepes, pH 7.4, 2 mM EDTA, 2 mM DTT, 0.1% CHAPS). After centrifugation, 20 µl of supernatant and 180 µl of reaction buffer (100 mM Hepes, pH 7.4, 2% of glycerol, 5 mM DTT, 0.5 mM EDTA, 50 µM DEVD-pNA (Biomol Research Laboratories)) were mixed and the absorbence at 405 nm was measured after incubating for four hours at 37° C. The anti-PARP polyclonal antibody SA-252 is marketed by Biomol Research Laboratories.

EXAMPLE 1

PML induces cell death independent of zVAD

Figure 1A:
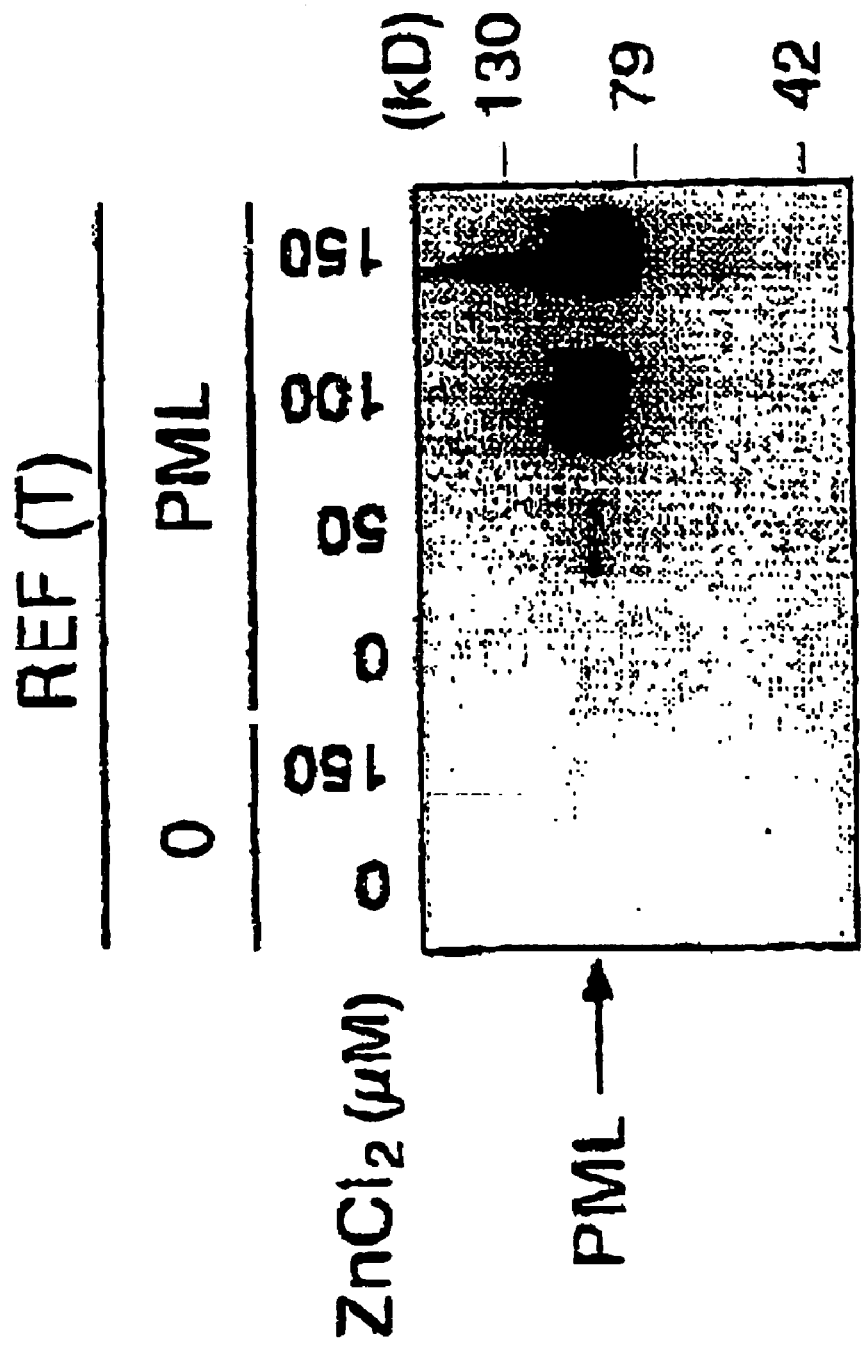
Figure 1B:
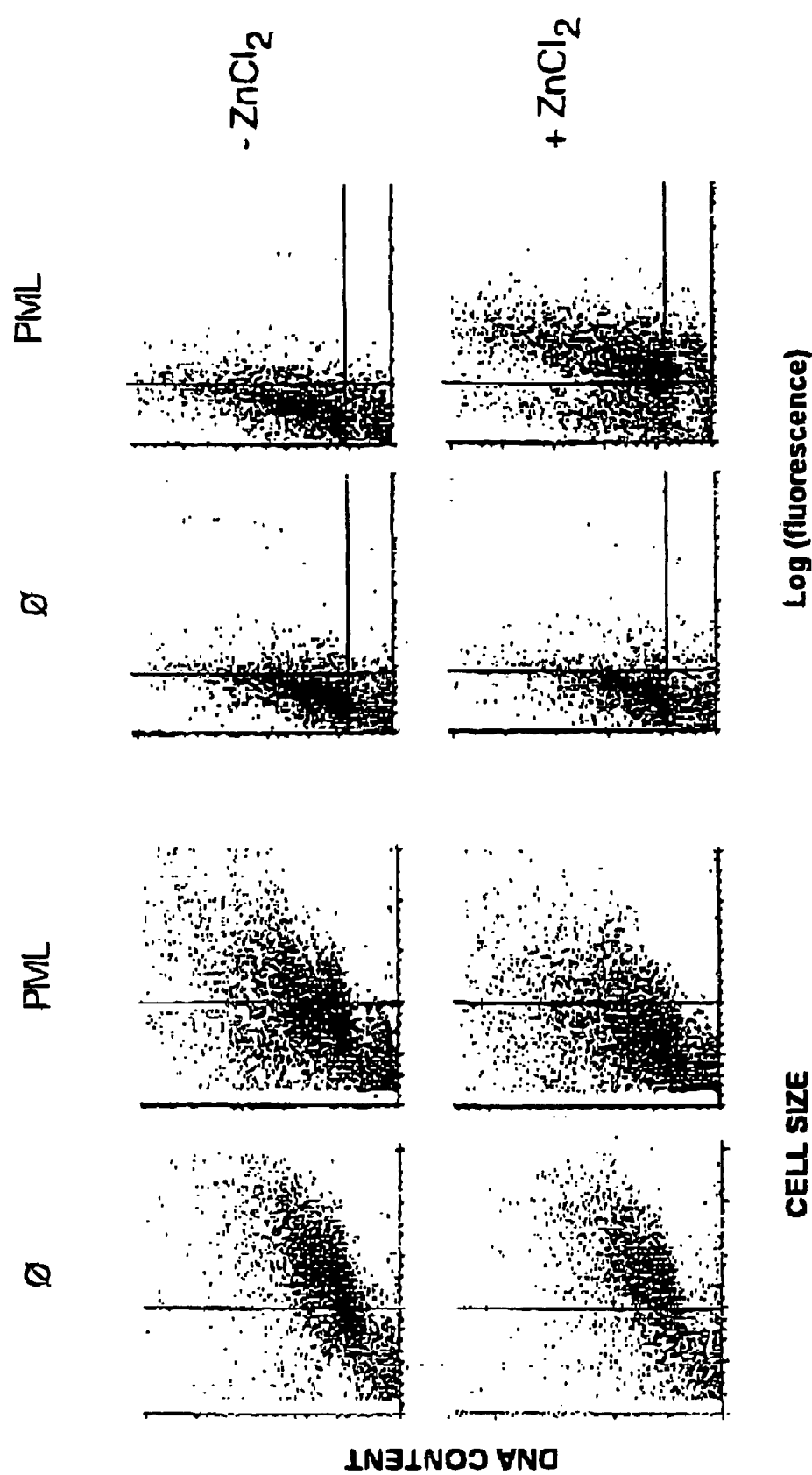
Figure 1C:
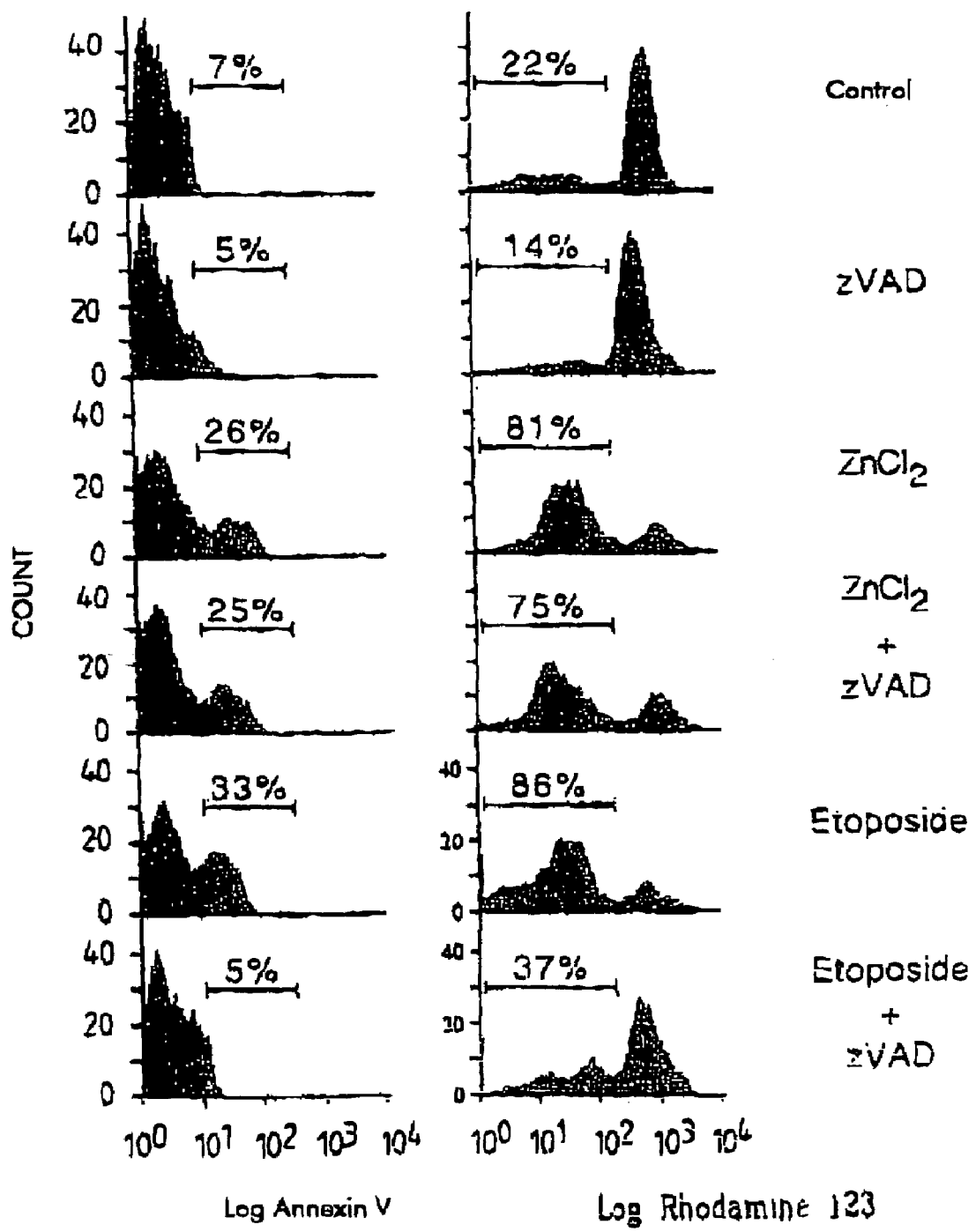

The transfection of a PML expression vector (pSG5-PML) into various fibroblast cell lines substantially reduced the formation of foci. The PML protein being undetectable in the clones obtained from the cells transfected with PML, these results mean that PML exerts a major inhibitory effect either on the cell cycle or on the survival of the cells. To understand the mechanism which forms the basis of this effect, a pool of rat embryo fibroblasts (REFs) transformed with SV40T was transfected with a plasmid pKSmMT-PML, in which the expression of PML is under the control of a mouse metallothionein promoter. Three of the resulting REF (T) PML clones were subsequently studied, whereas three RET (T) clones carrying the empty vector were tested as control. The PML protein was detected by Western blotting two hours after exposure to $ZnCl_2$ (expression detectable from 50 µM of $ZnCl_2$ and exhibiting a plateau at 150 µM of $ZnCl_2$) (FIG. 1A). The expression of PML induced a synchronized cell death of the whole cell population with kinetics varying from 48 hours for 50 µM of $ZnCl_2$ to six hours for 150 µM. In the three RET (T) PML clones, morphological modifications were observed from three hours after induction with 150 µM of $ZnCl_2$. The cells round up, with clear shrinkage of the cytoplasm (FIG. 1B), became positive in a TUNEL test (FIG. 1B) and then were progressively detached from the dish. They nevertheless retained their capacity to exclude trypan blue. These modifications were associated with a modest subG1 DNA content (FIG. 1B), an externalization of membrane phosphatidylserine (FIG. 1C) and a loss of mitochondrial transmembrane potential (FIG. 1C). While similar modifications were observed in apoptosis induced by the genotoxic agent etoposide, they were never found in the control REF (T) cells treated with $ZnCl_2$ (FIGS. 1B and C). Unlike the treatment with etoposide, the cell death induced by PML is not associated with nuclear morphological characteristics typical of apoptosis such as condensation of chromatin and nuclear fragmentation, even late, in the process of cell death. In spite of the cleavage of the DNA (positive sub-G1 (FIG. 1B) and loss of the viscosity of the DNA), the cell death induced by PML is not associated with an internucleosomal DNA scale, in conformity with the weak positive TUNEL signal (FIG. 1B).

Controls

As the REF (T) cells are cell lines transformed with SV40T, several experiments were carried out in order to exclude a contribution of the "large T" oncogene of the SV40 virus to the cell death induced by PML. Firstly, the expression of PML did not adversely affect the expression or the location of SV40T in the REF (T) PML cells nor did it degrade p53 or the release of p53 from the SV40 virus "large T" oncogene. Secondly, in the HeLa or CHO cells transiently transfected with either a fusion protein GFP-PML or GFP alone, all the GFP-PML positive cells gradually became detached from the dish and died, unlike the control GFP positive cells. Thirdly, in the CHO cells stably transfected with the plasmid pKSmMT-PML, the induction by $ZnCl_2$ here again led to the death of the clones expressing the PML protein. Finally, in the REF cells expressing a heat-sensitive SV40T mutant, the degradation of the SV40Ts at 39.5° C. did not affect the cell death triggered by PML.

The induction of cell death may require transcription de novo or may reflect the triggering of pre-existing pathways. The REF (T) PML cells were first of all incubated with $ZnCl_2$ and with cycloheximide for two hours, thus allowing the synthesis of mRNA for PML, and not its translation. The cells were then washed and incubated with actinomycin D alone in order to allow the translation of the mRNA for PML but not the mRNA neosynthesis. In this experiment, cell death was observed as in the absence of inhibitor, showing that transcription de novo is not required. Death induced by PML does not require and does not induce transition towards the S phase of the cell cycle. Indeed, PML always triggers death in the REF (T) PML cells which have been blocked at the G1/S stage by a treatment with aphidicolin. Furthermore, exposure to BrdU at various times after induction with $ZnCl_2$ showed that the replication of the DNA was not modified up to two hours but was stopped after three hours and that cell death was present in all the phases of the cell cycle (FIG. 1B).

EXAMPLE 2

Arsenic promot s cell death triggered by PML

When the REF (T) PML cells were treated with $ZnCl_2$ and $10^{-6}$ M $As_2O_3$, a strong acceleration in the morphological modifications associated with cell death was observed. The cleavage of the DNA, determined by TUNEL tests, increased in a similar manner (117% of positive cells for the cotreatment with $ZnCl_2$ against 45% for $ZnCl_2$ alone, whereas $As_2O_3$ alone did not induce any increase relative to the basal level). The fact that arsenic increases the induction of cell death in parallel with the location of PML on the nuclear bodies suggests that the location of PML near the nuclear bodies is important for cell death.

EXAMPLE 3

Death triggered by PML is not associated with the activation of caspases

Figure 2A:
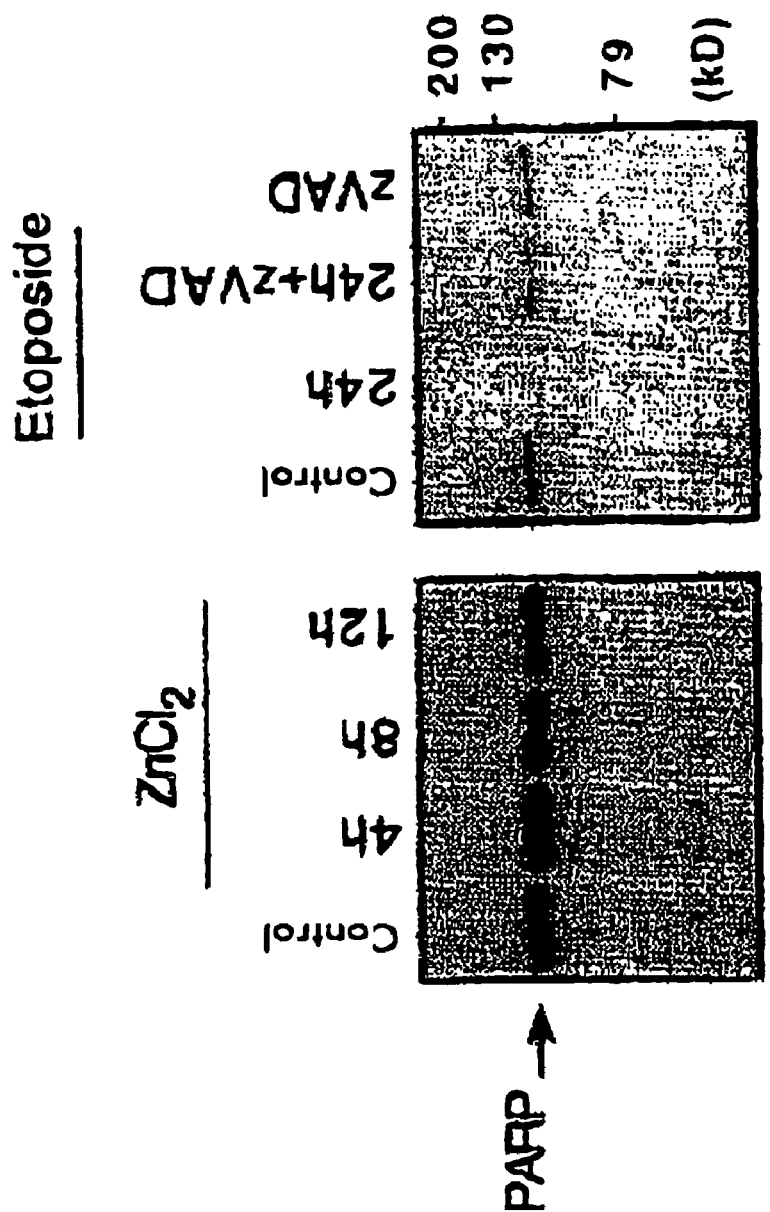
FIG. 2A represents the absence of cleavage of PARP during the cell death triggered by PML. The cells were treated with 150 μM $ZnCl_2$, etoposide or zVAD.
Figure 2B:
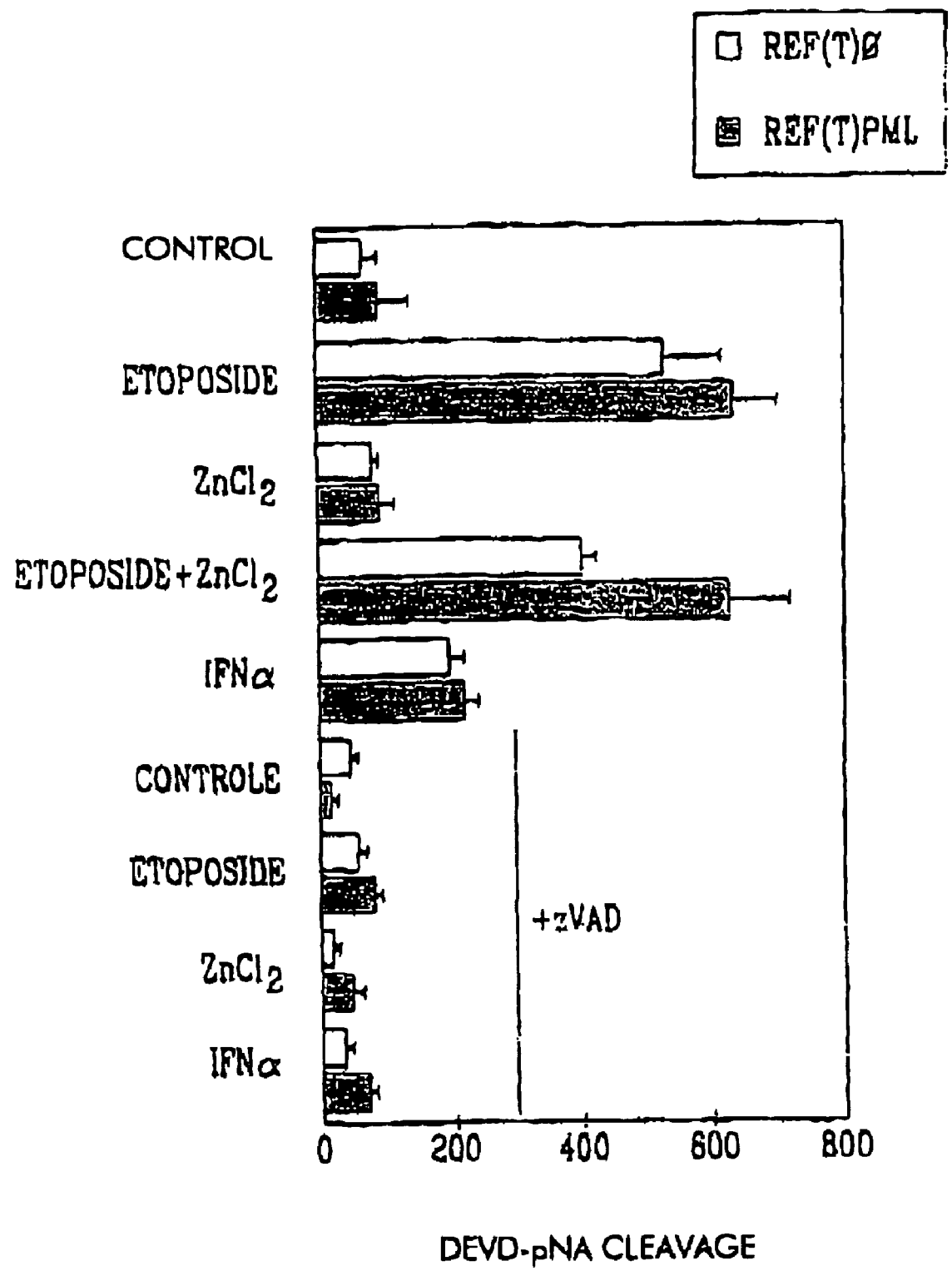
FIG. 2B represents the activity of the caspase CPP32 determined by cleavage of DEVD-pNA in control REF (T) cells or REF (T) PML cells. Relative absorbence values for three independent determinations are presented.

It is known that the execution of programmed cell death involves the proteolytic activation—of caspases which induce the phenotypic changes in apoptosis by cleavage of nuclear and cytoplasmic proteins (Salvesen et al., 1997). The caspase inhibitor zVAD, which blocks apoptosis induced by etoposide, does not inhibit cell death induced by PML (FIG. 1C) and even paradoxically accelerates it (71% of positive TUNEL signal with zVAD and $ZnCl_2$ against 45% $ZnCl_2$ alone). These observations mean that executing agents sensitive to zVAD are not required for cell death induced by PML. Furthermore, CPP32 (caspase 3), the principal caspase involved in apoptosis, appears not to be activated during cell death induced by PML since one of its substrates, PARP (poly(ADP-ribose)polymerase) remains noncleaved (FIG. 2A). Unlike etoposide, no significant cleavage of the colorimetric caspase substrates, YVAD-pNa (class 1 caspase, Boehringer Mannheim) and DEVD-pNA (class 3 caspase, Boehringer Mannheim) after induction with PML could be detected (FIG. 2B).

EXAMPLE 4

Arsenic and zVAD potentiate cell death induced by PML and interferons

Primary monocytes exposed to α-interferon were subjected to gradual cell death which led to the complete disappearance of the cell culture after seven days (FIGS. 3A and 3B). During the addition of zVAD with α-interferon, the death of the whole cell population was observed within 24 hours in the absence of nuclear fragmentation and of condensation of chromatin observed with interferon alone (FIGS. 3A and 3B). Little or no cell death was observed with zVAD alone for 20 days in most of the primary cultures (8/11) (FIGS. 3A and 3B). In three cultures out of eleven, zVAD alone induced the death of part of the culture after seven days, these results probably reflecting an endogenous secretion of interferon. Similar results were obtained with other caspase inhibitors such as DEVD.

The table below represents the cell death, evaluated by TUNEL, of REF (T) PML cells treated for two days with 1 000 U/ml of IFNα and $10^{-6}$ M of $As_2O_3$ or of zVAD.

|  | IFNα | |
| --- | --- | --- |
|  | − | + |
| Control | 5% | 42% |
| zVAD | 5% | 60% |
| $As_2O_3$ | 5.5% | 63% |

In the REF (T) cells, a substantial synergy was found between either α-interferon and zVAD, or α-interferon and $As_2O_3$ (42% of positive TUNEL signal for α-interferon alone, and 60% and 63% with zVAD and arsenic respectively).

zVAD increased the levels of expression of PML (FIG. 4A) and arsenic increased its association with the nuclear bodies, whereas the total quantity of PML was reduced. The similarity of the synergy of zVAD and arsenic with the cell deaths triggered by PML and interferon suggests that PML is involved with the cell death induced by interferon. Furthermore, α-interferon induces cell death with the same kinetics as 50 μM $ZnCl_2$ and the two induced similar quantities of PML protein (FIG. 4B).

The invention claimed is:

1. A method of inducing the death of adult T lymphoid leukemia (ATL) cells, comprising administering to a patient in need thereof amounts of a) arsenic trioxide or a caspase inhibitor selected from the group consisting of zVAD and DEVD; and b) an interferon, effective to synergistically induce the death of ATL cells.

2. The method of claim 1, wherein said interferon is selected from the group consisting of α-interferon, β-interferon and γ-interferon.

3. The method of claim 1, wherein said caspase inhibitor is zVAD.

4. The method of claim 1, wherein said caspase inhibitor is DEVD.

5. A method of treating or inhibiting adult T lymphoid leukemia, comprising administering to a patient in need thereof synergistically effective amounts of a) arsenic trioxide or a caspase inhibitor selected from the group consisting of zVAD and DEVD and b) an interferon to treat or inhibit adult T lymphoid leukemia.

6. The method of claim 5, wherein said interferon is selected from the group consisting of α-interferon, β-interferon and γ-interferon.

7. The method of claim 5, wherein said caspase inhibitor is zVAD.

8. The method of claim 5, wherein said caspase inhibitor is DEVD.

* * * * *